United States Patent [19]
Repschlager

[11] Patent Number: 5,207,661
[45] Date of Patent: May 4, 1993

[54] BODY FLUID DRAINAGE ASSEMBLY

[75] Inventor: Frank Repschlager, Burgdorf, Fed. Rep. of Germany

[73] Assignee: Smiths Industries Public Limited Company, London, England

[21] Appl. No.: 711,995

[22] Filed: Jun. 7, 1991

[51] Int. Cl.$^5$ .................... A61M 1/00; A61B 5/00
[52] U.S. Cl. .................... 604/317; 604/323; 604/324; 604/325; 604/326; 604/327; 128/748; 128/760
[58] Field of Search ............ 604/317, , 322, 323, 604/324, 326, 327, 318, 319, 320, 321, 126, 128, 276, 277, 333, 338, 406, 127, 246, 247, 250, 251, 253, 254; 128/767, 768, 760, 748

[56] References Cited

U.S. PATENT DOCUMENTS

| Re. 26,964 | 10/1970 | Coanda | 604/324 |
|---|---|---|---|
| 3,583,401 | 6/1971 | Vaillencourt et al. | |
| 3,604,420 | 9/1971 | vAILLENCOURT | |
| 3,661,143 | 5/1972 | Henken | |
| 3,727,603 | 4/1973 | Holbrook | 604/335 |
| 3,838,691 | 10/1974 | Paludan | 604/324 |
| 3,906,935 | 9/1975 | Raia et al. | |
| 3,957,050 | 5/1976 | Hines, Jr. | 604/128 |
| 3,965,895 | 6/1976 | Dabney | 604/127 |
| 4,366,836 | 1/1983 | Villari | 604/324 |
| 4,465,479 | 8/1984 | Meisch et al. | |
| 4,500,311 | 2/1985 | Redmond et al. | 604/325 |
| 4,512,771 | 4/1985 | Norton | 604/324 |
| 4,621,647 | 11/1986 | Loveland | 128/748 |
| 4,696,672 | 9/1987 | Mochizuki et al. | 604/128 |
| 4,731,056 | 3/1988 | Tremulis | 604/326 |
| 4,858,619 | 8/1989 | Toth | 128/748 |
| 4,863,447 | 5/1989 | Smith | 604/324 |

FOREIGN PATENT DOCUMENTS 2031282 4/1980 United Kingdom ............... 604/335

OTHER PUBLICATIONS

Cordis External Ventricular Drainage Set, 1 pg., 1974

Primary Examiner—Randall L. Green
Assistant Examiner—K. M. Reichle
Attorney, Agent, or Firm—Pollock, Vande Sande & Priddy

[57] ABSTRACT

An assembly for collecting body fluids, especially cerebro-spinal fluids, which includes a drip chamber having an upper portion for introducing therein fluids to be collected and a lower portion, including a drainage tube, for draining fluids therefrom. The upper portion is provided with an overflow tube which is connected to the drainage tube and an air vent which is connected to a biological filter. The air vent comprises a tubular member and a device for closing the passageway in the tubular member to prevent fluid from wetting the biological filter.

1 Claim, 1 Drawing Sheet

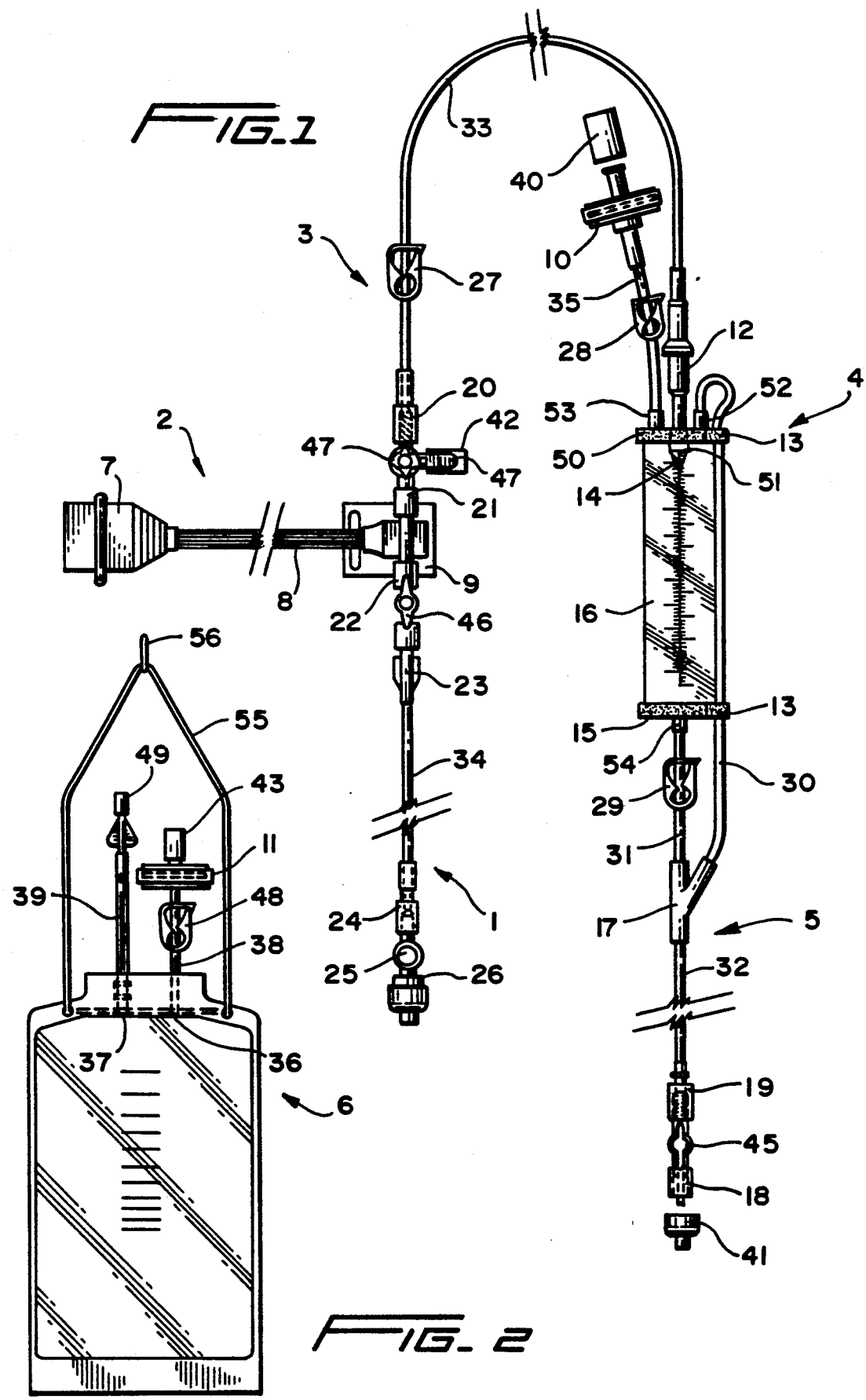

5,207,661

BODY FLUID DRAINAGE ASSEMBLY

The present invention relates generally to medical devices for draining fluids from a patient.

BACKGROUND OF THE INVENTION

Medical procedures for draining fluids from a patient require care to prevent infection, and may require control of the drainage rate and/or control of pressure of the fluid within the patient. Devices to prevent infection and to control fluid flow rate and pressure are especially important in carrying out procedures for draining excess cerebro-spinal fluid (CSF) from the ventricles of a patient's brain, since if the pressure of the CSF is either too high or too low, the result may be permanent injury or death.

In a typical CSF drainage system, a drip chamber is interposed between a drainage tube extending from a patient and a collection vessel in order to provide a break in the flow path of the liquid and thereby prevent backward movement of microbes which may be present. If the chamber overflows, there is a danger that a path will be provided for movement to the patient of microbes which may be present.

These prior art devices typically include a vent device at the top of the drip chamber to prevent a buildup of pressure. The vent may be provided with a filter to prevent contamination of the system; however, there is danger that pressure will increase within the drip chamber if the filter becomes wet, which may result from fluid overflow or fluid which splashes within the drip chamber.

SUMMARY OF THE INVENTION

It is accordingly one object of the present invention to provide improved means for preventing a fluid collection chamber in a fluid drainage system from overfilling.

It is another object of the present invention to provide an improved air venting device for a fluid collection chamber. Other objects will become apparent from the following description and the claims appended hereto.

In accordance with the present invention, there is provided an assembly for collecting body fluids comprising a fluid collection chamber having upper and lower end portions; fluid inlet means, gas venting means, and fluid overflow means operatively connected to the upper end portion of the fluid collection chamber; fluid outlet means operatively connected to the lower end portion of the fluid collection chamber for draining fluid from the chamber; and bypass means operatively connecting the fluid overflow means in the top portion of the fluid collection chamber with the fluid outlet means in the bottom portion of the fluid collection chamber.

In another aspect of the invention, a gas venting means for a collection chamber comprises a biological filter in fluid communication with the upper end portion of the fluid collection chamber and means for isolating the biological filter from the upper end portion for selectively preventing the flow of fluid between the collection chamber and the filter.

In a preferred embodiment of the present invention, such as may be used in CSF collection procedures, the fluid collection assembly includes both the overflow bypass feature and means for preventing flow of liquid from the collection chamber to a biological filter. The present invention is particularly useful in medical procedures which require close control of fluid pressures such as, for example, procedures for draining CSF from a patient.

BRIEF DESCRIPTION OF THE DRAWING

FIG. 1 is an elevational view of a drainage system including a cerebral-spinal fluid collection assembly of the present invention.

FIG. 2 is an elevational view of a collection vessel including an embodiment of the present invention.

DETAILED DESCRIPTION OF THE INVENTION

The present invention is useful in carrying out a variety of surgical procedures which require that fluid be drained from a patient; however, the present invention is particularly useful in draining CSF from a patient, and it will be described in detail with respect to a drainage system which is adapted for that purpose.

With reference to the drawings, the drainage system depicted therein comprises, in sequence according to the flow of CSF from a patient to a collection vessel, a fluid flow assembly 1 leading from a cannula within a patient (not shown), a pressure transducer assembly 2, a fluid flow assembly 3, a drip chamber assembly 4, a fluid flow assembly 5, and a collection vessel assembly 6.

Fluid flow assembly 1 is adapted for fluid communication with a drainage catheter, such as those which are well-known to those skilled in the art. A suitable drainage catheter may be connected to fluid flow assembly 1 through various arrangements of tubing, valves and connections such as those described in U.S. Pat. Nos. 3,957,050 to Hines, Jr., and 4,500,311 to Redmond et al.

Fluid flow assembly 1 includes a sampling fitting 26 having a diaphragm 25 for insertion therethrough of a needle (not shown) for withdrawing a sample of CSF fluid. Tube 34 is connected at one end to sampling fitting 26 by a connector 24 and at the other end to a pressure transducer 9 through a connector 23, a two-port valve 46, and a connector 22.

Transducer assembly 2 comprises pressure transducer 9 for generating a signal which is responsive to the pressure of CSF in the fluid line. A cable 8 leads to an electrical connector 7 which is adapted for connection with means (not shown) for responding to the signal generated by transducer 9. Pressure transducer assemblies suitable for use in a CSF drainage system are well-known to those skilled in the art.

Fluid flow pathway 3, which comprises a tube 33 and associated fittings, communicates at its upstream end with pressure transducer 9 and at its downstream end with drip chamber assembly 4. The upstream end of fluid flow pathway 3 is connected to pressure transducer 9 by a connector 21, a three port valve 47 and a connector 20. Valve 47 is provided with a removable closure cap 42 for closing the port in member 47'. Fluid flow pathway 3 is connected at its downstream end with drip chamber 4 by a connector 12, preferably made of a flexible material such as latex. A clamp 27 is provided for compressing the walls of tube 33 and thus blocking the flow of fluid therethrough as needed.

Drip chamber assembly 4 comprises an elongated graduated transparent cylinder 16, preferably made of a rigid plastic, and associated components. Cylinder 16 is provided with a bottom wall 15 having an outlet port 54 and a top wall 50 with a fluid inlet port 51, an overflow port 52, and an air vent port 53. Inlet port 51 is provided within cylinder 16 with a one-way duckbill valve 14. Air vent port 53 is connected to a biological filter assembly 10 through a flexible, compressible tube 35 which is provided with clamping means 28 for preventing flow of fluid to biological filter 10 when activated. Vent cap 40 is secured to the outer end of biological filter assembly 10 and is provided with a passage (not shown) for air flow. Clamp 28 provides a simple, positive and economical method for keeping the biological filter dry when there is a possibility of liquid flowing upwardly through port 53 and into tube 35.

Straps 13 are provided at the upper and lower end portions for securing cylinder 16 to a support member (not shown). Straps 13, which also keep overflow tube 30 in position against the outer surface of cylinder 16, preferably are provided with surfaces which fasten together, such as a pressure-sensitive adhesive-covered surface or VELCRO ® type bonding.

An overflow tube 30 connects overflow port 52 with a drip chamber outlet tube 31, at a Y connector 17 in fluid flow assembly 5. Fluid flow assembly 5 comprises outlet tube 31 which is connected to outlet port 54, Y-connector 17, a tube 32, a connector 19, a two port valve 45, a connector 18, and an end cap 41. Tube 31 is also provided with a clamp 29 for optionally preventing fluid flow through tube 31.

FIG. 2 shows graduated collection vessel 6 which is provided at a upper portion with ports 36 and 37 connected respectively to an air vent tube 38 and a fluid inlet tube 39. Inlet tube 39 is provided at its upper portion with connector 49 for joining with connector 18 in fluid flow assembly 5. Tube 38 is provided with clamp means 48 for preventing the flow of fluid through line 38 when activated. Biological filter assembly 11 is secured to the outer end portion of air vent tube 38, and is provided with vent cap 43. Collection vessel 6 can be suspended from a support (not shown) by flexible cord 55 and hook 56.

Tube 34 and other tubes in the system are preferably of the type used in intravenous applications and are well-known in the art. More specifically, the tubes are preferably formed from a flexible transparent plastic material, and have a small diameter. The members which connect together tubes, valves and various other components are well-known to those skilled in the art and may be provided with slip fit, twist lock or screw type mating portions. Any suitable valve which opens and closes the assembly to fluid flow may be used and may be either a two- or three-port valve, such as are shown in the drawing.

The overflow feature of the drip chamber and the means for preventing flow of fluid through a tube to the biological filter in the air vent may be used separately or together; however, in the preferred assembly for carrying out CSF drainage procedures both features are used on the drip chamber assembly, and the air vent feature is used on the collection vessel.

The foregoing description is intended to illustrate, and not to limit the present invention, and variations thereof may occur to those skilled in the art. For example, the features of the present invention may be used in collecting body fluids other than CSF and various modifications may be made in the apparatus. For instance, the presence of a pressure transducer is preferred in an assembly for collecting cerebro-spinal fluids but may not serve any useful purpose for some other drainage procedures.

What is claimed is:

1. An assembly for draining cerebro-spinal fluid from a human body comprising:
    (a) a graduated drip chamber having a top wall, a bottom wall, a peripheral wall extending between said top and bottom walls, cerebro-spinal fluid inlet means including a one-way valve for introducing cerebro-spinal fluid into said drip chamber, yet preventing cerebro-spinal fluid from flowing from said drip chamber toward said human body, said one-way valve positioned within said drip chamber below the top wall fluid overflow outlet means including a fluid passageway in said top wall for passing fluid upwardly through said top wall to remove overflow fluid from said drip chamber, when the level of said cerebro-spinal fluid within said drip chamber reaches the top wall and cerebro-spinal fluid outlet means operatively connected to said bottom wall for draining cerebro-spinal fluid from said drip chamber;
    (b) an elongated flexible tubular member operatively connected to said fluid inlet means for introducing cerebro-spinal fluid from said human body into said drip chamber;
    (c) cerebrospinal fluid pressure monitoring means operatively connected to said elongated flexible tubular member;
    (d) tubular drainage means operatively connected to said fluid outlet means at said bottom wall for draining cerebro-spinal fluid from said drip chamber;
    (e) fluid overflow bypass tube means operatively connecting said fluid overflow outlet means in said top wall with said tubular drainage means for transferring overflow fluid from said fluid overflow outlet means to said tubular drainage means; and,
    (f) gas venting means comprising a flexible, compressible gas outlet tube operatively connected to said top wall for releasing gas from said chamber, a biological filter operatively connected to said gas outlet tube and spaced apart from said top wall, and tube clamping means operatively connected to said gas outlet tube between said filter and said top wall for compressing said gas outlet tube and preventing the flow of fluid between said chamber and said filter when activated.

* * * * *